United States Patent
Zhang et al.

(10) Patent No.: US 11,655,313 B2
(45) Date of Patent: May 23, 2023

(54) PEPTIDE-CROSSLINKED PROTEIN-IMPRINTED POLYMERS AND PREPARATION METHOD AND APPLICATIONS THEREOF

(71) Applicant: NANKAI UNIVERSITY, Tianjin (CN)

(72) Inventors: Yongjun Zhang, Tianjin (CN); Rong Xu, Tianjin (CN); Ying Guan, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 0 days.

(21) Appl. No.: 16/954,644

(22) PCT Filed: Apr. 19, 2019

(86) PCT No.: PCT/CN2019/083343
§ 371 (c)(1),
(2) Date: Jun. 17, 2020

(87) PCT Pub. No.: WO2020/172973
PCT Pub. Date: Sep. 3, 2020

(65) Prior Publication Data
US 2021/0388123 A1    Dec. 16, 2021

(30) Foreign Application Priority Data

Feb. 28, 2019  (CN) .......................... 201910147938.9

(51) Int. Cl.
*C08F 2/44*  (2006.01)
*C08F 2/04*  (2006.01)
(Continued)

(52) U.S. Cl.
CPC .................. *C08F 2/44* (2013.01); *C08F 2/04* (2013.01); *C08F 220/06* (2013.01); *C08F 220/56* (2013.01); *C08F 289/00* (2013.01)

(58) Field of Classification Search
CPC .. C08F 2/44; C08F 2/04; C08F 220/06; C08F 220/56; C08F 289/00
See application file for complete search history.

(56) References Cited

U.S. PATENT DOCUMENTS 6,852,818 B1 * 2/2005 Piletsky ............... C07K 14/001
526/303.1
2006/0240435 A1  10/2006  Minoura et al.

FOREIGN PATENT DOCUMENTS

CN          108752524 A  * 11/2018  ............ B01J 20/268

OTHER PUBLICATIONS

English translation of CN 108752524A. (Year: 2018).*
(Continued)

*Primary Examiner* — Catherine S Branch
(74) *Attorney, Agent, or Firm* — Nolte Lackenbach Siegel (57) ABSTRACT

A peptide-crosslinked protein-imprinted polymer, preparation method, and application thereof. One method comprises: 1) dissolving a main monomer, functional monomers, a peptide crosslinking agent, and a template protein in an aqueous solution to obtain a mixed solution; 2) adding an initiator or initiator system to the mixed solution to initiate the polymerization when the peptide crosslinking agent exists in a helix conformation to obtain a polymer; 3) eluting the template protein when the peptide chain exists in a coil conformation to obtain a peptide-crosslinked protein-imprinted polymer. The peptide crosslinking agent is a peptide with a polymerizable double bond at its both ends, and being capable of undergoing helix-coil transition. The polypeptide crosslinking agent is a polypeptide having an amino acid sequence which has a polymerizable double bond at its both ends, being capable of undergoing a helix-coil conformational transformation. The polypeptide cross-linked protein molecule-imprinted polymer disclosed in the invention not only can completely remove the template protein under mild
(Continued)

conditions, but also can significantly improve the imprint effect of the protein molecule-imprinted polymer.

10 Claims, 3 Drawing Sheets

(51) Int. Cl.
*C08F 220/06* (2006.01)
*C08F 220/56* (2006.01)
*C08F 289/00* (2006.01)

(56) References Cited

OTHER PUBLICATIONS

Matsumoto, et al. "Conformationally Regulated Molecular Binding and Release of Molecularly Imprinted Polypeptide Hydrogels That Undergo Helix-Coil Transition" in American Chemical Society, 2017, 50, 2136-2144.
Chen, et al. "Protein-responsive imprinted polymers with specific shrinking and rebinding" in Journal of Molecular Recognition, 2008; 21: 71-77.
Culver, et al. "Protein-Imprinted Polymers: The Shape of Things to Come?" in American Chemical Society, 2017, 29, 5753-5761.

\* cited by examiner

PEPTIDE-CROSSLINKED PROTEIN-IMPRINTED POLYMERS AND PREPARATION METHOD AND APPLICATIONS THEREOF

CROSS-REFERENCE TO RELATED APPLICATIONS

This Application is a 371 Application of International Patent Application Serial No. PCT/CN2019/083343, entitled, "POLYEPTIDE CROSSLINKED PROTEIN MOLECULAR IMPRINTING POLYMER, PREPARATION METHOD THEREFOR, AND APPLICATION THEREOF, filed Apr. 19, 2019. The application claims priority of China patent application No. 201910147938.9, names" Peptide-crosslinked Protein-imprinted Polymers And Preparation Method And Applications Thereof", filed Feb. 28, 2019 to National Intellectual Property Administration, PRC, which is incorporated by reference in the application in its entirety.

CROSS-REFERENCE TO RELATED APPLICATIONS

The application claims the priority of China patent application No. 201910147938.9, named "Peptide-crosslinked Protein-imprinted Polymers And Preparation Method And Applications Thereof", filed on Feb. 28, 2019 to National Intellectual Property Administration, PRC, which is incorporated by reference in the application in its entirety.

TECHNICAL FIELD

The invention belongs to the technical field of bioseparation engineering, and especially relates to peptide-crosslinked protein-imprinted polymers and preparation method and applications thereof.

BACKGROUND

Molecularly imprinted polymers are a class of artificial receptors inspired by antibody which can recognize antigen specifically. Molecularly imprinted polymers have benefits such as simple preparation, good stability and low cost as compared to natural receptors like antibody, playing a significant role in the field of environmental science, life science, etc. The general processes of molecular imprinting are as follows: (1) the polymer is synthesized by polymerization of monomers and cross-linkers in the presence of template molecules; (2) the template is removed, leaving imprint cavities, which are chemically and sterically complementary to the template molecule, in the polymer; (3) the imprinted polymer recognizes and selectively recombines target molecules when exposed to a solution containing the template molecules.

The imprinting of low molecular-weight compounds has gained great success. However, the imprinting of high molecular-weight biomacromolecules, particularly proteins, still faces many challenges. The first problem faced by protein imprinting is the difficulty in template removal. The high molecular weights of the template proteins severely retard their diffusion through the dense polymer networks. Presently, the template proteins were usually removed by harsh methods, for example, elution using high concentration salt solutions (e.g. 1M NaCl) or mixed solutions of acetic acid/surfactant (SDS or Tween-20) (a common formula is 10% SDS/10% AcOH). Proteinase is also used to digest template proteins for removing these template proteins.

These treatments cannot guarantee a complete removal of the template proteins, and often cause problems such as changes in structure of the imprinted polymer networks, non-specific adsorption of the proteins, and blockage of the imprinting sites. More importantly, the stringent elution conditions are so easy to cause denaturation and deactivation of the template proteins that the eluted target proteins lose their use values, while the method by digestion with proteinase directly destroys the template proteins. In many applications of protein imprinting, such as enrichment, separation and purification of proteins, it is necessary to recover active target proteins, so the harsh elution conditions make such imprinted polymers largely lose their application values.

A second serious problem of protein imprinting is a poor imprint effect. Proteins are only soluble in water and are easy to denature and deactivate, so the organic solvents often used in the imprinting of low molecular weight compounds are not applicable, and the imprinting of protein can be only performed in an aqueous solution. On the one hand, this limits the selection of monomer; on the other hand, the presence of water weakens the hydrogen bonding between the template and the functional monomer, resulting in a reduction of acting force between the template and the functional monomer. To recognize the target molecule, the size and spatial configuration of imprinting sites in the polymer must be kept unchanged. Therefore, the degree of cross-linking of the polymer in small molecule imprinting is often up to more than 50%. However, in protein imprinting, the templates are so difficult to remove that a low degree of cross-linking can only be used. Given these reasons, the imprinting effect of existing protein-imprinted materials is not ideal. For example, Chen, et al. disclosed an imprinted polymer using lysozyme as the template protein, the imprinted polymer was polymerized by using N-isopropylacrylamide as the main monomer, methacrylic acid and acrylamide as the functional monomers, and N,N'-methylenebisacrylamide as cross-linker whose content was 3.11 mol %. The template protein was eluted by using 1M NaCl. The imprinting capacity Qm was 350 mg/g dry gel and the imprinting factor was 1.167 (Z. Chen, et al. Journal of Molecular Recognition, 2008, 21(1), 71-77).

For protein imprinting, the problems of difficulty in template removal and poor imprint effect seem to be intrinsic problems, and these two problems are mutually restrained and difficult to solve at the same time. A long-term study still does not find an effective method to solve these problems, casting a shadow on the prospect of protein imprinting. (Culver, H. R.; Peppas, N. A., Chemistry of Materials, 2017, 29(14), 5753-5761).

SUMMARY

In view of this, the objective of the invention is to provide peptide-crosslinked protein-imprinted polymers and preparation method and applications thereof.

To achieve the above-mentioned objective of the invention, the invention provides the following technical solutions:

A preparation method of peptide-crosslinked protein-imprinted polymer comprising the steps of:
  1) a main monomer, functional monomers, a peptide crosslinking agent and a template protein are dissolved in an aqueous solution to obtain a mixed solution;

2) an initiator or initiator system is added to the mixed solution described in the step 1) to initiate the polymerization when the peptide crosslinking agent exists in a helix conformation, thereby obtaining a polymer;

3) the template protein is eluted when the peptide chain exists in a coil conformation and a peptide-crosslinked protein-imprinted polymer is obtained;

wherein the peptide crosslinking agent is a peptide with a polymerizable double bond at its both ends, and being capable of undergoing helix-coil transition.

Preferably, the number of amino acids in the peptide crosslinking agent is 2 to 100.

Preferably, the number of amino acids in the peptide crosslinking agent is 5 to 30. Preferably, the water-soluble solvent described in the step 1) includes one of phosphate buffer, Tris buffer and $NaClO_4$ solution.

Preferably, the mass ratio of the main monomer:the functional monomer:the peptide crosslinking agent:the template protein described in the step 1) is (10-30):(0.5-2):(5-20):(5-20).

Preferably, the initiator is selected from ammonium persulfate/tetramethylethylenediamine, ammonium persulfate/sodium bisulfite, potassium persulfate/tetramethylethylenediamine, and potassium persulfate/sodium bisulfite.

Preferably, the conformational state of the peptide crosslinking agent is detected by circular dichroism, in which CD spectrum presents a negative peak at 222 nm and 208 nm, and a positive peak at 190 nm±5 nm representative of a helix conformation; also, CD spectrum presents a negative peak at 199 nm, and a positive peak at 220 nm±5 nm representative of a coil conformation.

The invention provides a peptide-crosslinked protein-imprinted polymer prepared by said preparation method.

The invention provides the application of said peptide-crosslinked protein-imprinted polymer in protein enrichment, separation, and purification.

Preferably, the peptide-crosslinked protein-imprinted polymer is used to adsorb target protein when the peptide crosslinking agent exists in a helix conformation and to elute target protein when the peptide crosslinking agent exists in a coil conformation.

The benefits of the invention: The peptide crosslinking agent can transit between different conformations in response to changes in external conditions. Given this special property, the preparation method of peptide-crosslinked protein-imprinted polymer provided in the invention uses the peptide crosslinking agent instead of traditional crosslinking reagent (such as N,N'-methylenebisacrylamide) to conduct polymerization when the peptide crosslinking agent exists in a helix conformation and template elution when the peptide crosslinking agent exists in a coil conformation. When the peptide crosslinking agent transits from a helix conformation to a coil conformation, the protein-imprinted polymers swell which facilitates the removal of the template protein. Therefore the removal of template proteins under mild conditions is achieved. When the peptide-crosslinked protein-imprinted polymer is applied, the peptide crosslinking agent is re-transformed from a coil conformation to a helix conformation by adjusting external environmental parameters, and the whole protein-imprinted polymer shrink; more importantly, since the conformation transition is highly specific when peptide folds back from a coil conformation into a helix conformation, the size and shape of the imprint cavities in the protein-imprinted polymer can completely recover and thus can specifically recognize the target protein.

The peptide-crosslinked protein-imprinted polymer provided in the invention not only can completely remove the template protein under mild conditions, but also can significantly improve the imprint effect of the protein-imprinted polymer. According to the description of example 1, the method described in the invention was used to prepare the protein-imprinted polymer which had the same formula with the protein-imprinted polymer with lysozyme as template described in the reference (Z. Chen, et al. Journal of Molecular Recognition, 2008, 21(1), 71-77), in which the content of the cross-linking reagent was still 3.1 mol %, but the common cross-linking reagent N,N'-methylenebisacrylamide was replaced by the peptide crosslinking agent described in example 1. The template protein was removed completely by elution with a pH 7.4 phosphate buffer (containing 0.154M NaCl). Protein rebinding demonstrated that the adsorption capacity Qm and imprinting factor of the newly synthesized imprinted polymers were 679 mg/g dry gel and 10.0, respectively, while the adsorption capacity Qm and imprinting factor of the imprinted polymer described in the reference (Z. Chen, et al. Journal of Molecular Recognition, 2008, 21(1), 71-77) were 350 mg/g dry gel and 1.167, respectively. As compared to the reference, the imprint effect of the peptide-crosslinked imprinted polymer was improved significantly.

DESCRIPTION OF THE EMBODIMENTS

The invention provides a preparation method of peptide-crosslinked protein-imprinted polymer, which comprises the steps of: 1) a main monomer, functional monomers, a peptide crosslinking agent and a template protein are dissolved in an aqueous solution to obtain a mixed solution; 2) an initiator or initiator system is added to the mixed solution described in the step 1) to initiate the polymerization when the peptide crosslinking agent exists in a helix conformation, thereby obtaining a polymer; 3) the template protein is eluted when the peptide chain exists in a coil conformation and a peptide-crosslinked protein-imprinted polymer is obtained; the peptide crosslinking agent is a peptide with a polymerizable double bond at its both ends, and being capable of undergoing helix-coil transition.

In the invention, the peptide crosslinking agent is a peptide with a polymerizable double bond at its both ends, and being capable of undergoing helix-coil transition. In the invention, the helix-coil transition preferably occur under different conditions; during the detailed implementation of the invention, the helix-coil transition may be triggered by temperature change, pH value change, and ionic strength change, etc. The invention poses no special requirements on the conditions of helix-coil transition, and these conditions are determined depending on the type of different peptide crosslinking agents, as long as the helix-coil transition can be achieved. In the invention, the conformation of the peptide chain is detected by circular dichroism, in which CD spectra present a negative peak at 222 nm and 208 nm, and a positive peak at 190 nm±5 nm representative of a helix conformation; also, CD spectrum presents a negative peak at 199 nm, and a positive peak at 220 nm±5 nm representative of a coil conformation.

The invention poses no special requirements on the number, type, and sequence of amino acids in said peptide crosslinking agent, and any peptide with a polymerizable double bond at its both ends, and being capable of undergoing helix-coil transition can be used as the peptide crosslinking agent described in the invention. During the detailed implementation of the invention, the number of amino acids in the peptide crosslinking agent is 2 to 100, preferably 5 to 30. The peptide crosslinking agent described in the present embodiment can be selected from the peptides having a structure of formula I to VI described below:

The invention dissolves a main monomer, functional monomers, a peptide crosslinking agent and a template protein in an aqueous solution to obtain a mixed solution. The invention poses no special requirements on the type of the main monomer and functional monomers, and the conventional main monomers and functional monomers used in the preparation of protein-imprinted polymers in the art may be used. The invention poses no special requirements on the type of template proteins, any type of proteins can be used as the template protein. In the invention, the aqueous solution preferably includes but are not limited to one of phosphate buffer, Tris buffer and NaClO$_4$ solution; and the preferred concentration and pH value of the aqueous solution described in the invention are determined depending on the type of the aqueous solution and the specific type of the peptide crosslinking agent. When the aqueous solution is phosphate buffer, the concentration of the phosphate buffer is preferably 1-100 mmol/L, more preferably 10-20 mmol/L, and the pH value of the phosphate buffer is preferably 5.0-5.6. When the aqueous solution is Tris buffer, the concentration of the phosphate buffer is preferably 1-50 mmol/L, more preferably 10-20 mmol/L, and the pH value of the Tris buffer is 7.0-10. When the aqueous solution is NaClO$_4$ solution, the concentration of the NaClO$_4$ solution is 0.05-0.50 mol/L, more preferably 0.1-0.3 mol/L. In the invention, the mass ratio of the main monomer:the functional monomers:the peptide crosslinking agent:the template protein is preferably (10-30):(0.5-2):(5-20):(5-20). In the invention, the ratio of total mass of the main monomer, the functional monomers, the peptide crosslinking agent, and the template protein to the volume of the aqueous solution is preferably (1-5):(5-15).

In the invention, an initiator is added to the mixed solution after obtaining the mixed solution to polymerize when the peptide crosslinking agent exists in a helix conformation, thereby obtaining a polymer. In the invention, the initiator or initiator system is preferably selected from ammonium persulfate/tetramethylethylenediamine, ammonium persulfate/sodium bisulfite, potassium persulfate/tetramethylethylenediamine, and potassium persulfate/sodium bisulfite; more preferably, ammonium persulfate/tetramethylethylenediamine. When ammonium persulfate/tetramethylethylenediamine are selected as the initiator, the mass concentration of the ammonium persulfate solution is preferably 1-20%, more preferably 5-10%, and the volume ratio of the ammonium persulfate solution to tetramethylethylenediamine is preferably (8-12):1, more preferably 10:1. In the invention, the volume ratio of the mixed solution to the initiator is preferably (25-50):(1-5). In the invention, the polymerization time is preferably 20-28 h, more preferably 24 h; and the polymerization temperature is adjusted correspondingly depending on the type of the specific peptide crosslinking agent to enable the peptide crosslinking agent exists in a helix conformation.

In the invention, after obtaining the polymer, the template protein is removed when the peptide chain exists in a coil conformation to obtain a peptide-crosslinked protein-imprinted polymer. In the invention, the eluent used in elution is preferably consistent with the corresponding aqueous solution, and the pH or temperature of the elution is different from that during the polymerization. The invention poses no special requirements on elution conditions, as long as these conditions enable the peptide chain exists in a coil conformation.

The invention provides peptide-crosslinked protein-imprinted polymers prepared by said preparation method.

The invention provides applications of said peptide-crosslinked protein-imprinted polymer in protein enrichment, separation and purification. In the detailed implementation of the invention, the peptide-crosslinked protein-imprinted polymer is used to adsorb target protein when the peptide chain exists in a helix conformation and target protein is eluted when the peptide chain exists in a coil conformation.

The following described the technical solutions provided in the invention in detail in combination with embodiments, but should not be understood as limiting the protection scope of the invention.

Example 1

The synthesis of imprinted polymers:
200 mg of N-isopropylacrylamide, 5 mg of acrylamide, 4 µL of methacrylic acid, 115 mg of the peptide crosslinking agent, and 100 mg of template protein lysozyme were dissolved in 2 mL of a 20 mM pH 5.5 phosphate buffer solution. After thorough mixing, 50 µL of 10% APS and 5 µL of TEMED were added to initiate polymerization, and the reaction was carried out at 37° C. for 24 hours to obtain the imprinted polymer MIP. The preparation of non-imprinted polymer NIP is the same as that of imprinted polymer, except that no template protein lysozyme is added. The structure of the peptide crosslinking agent is as shown in Formula I:

The Elution of Template Protein:
Protein elution was performed at 37° C. with a 20 mM pH 7.4 phosphate buffer solution (containing 0.154 M NaCl to simulate a physiological ionic strength). The absorbance values of eluent were determined, and an ultraviolet spectrophotometer was used to draw a standard curve of absorbance-concentration of target protein at specific wavelengths. The absorbance values of protein solution were converted into concentration values according to the standard curve. The results were as follows: 100 mL of the eluent was used each time. The concentration of template protein in the eluent after the first elution was 0.927 mg/mL; the concentration of template protein in the eluent after the second elution was 0.0474 mg/mL; the concentration of template protein in the eluent after the third elution was 0.0037 mg/mL; while the template protein was not detected in the eluent by an ultraviolet spectrophotometer after the fourth elution. Elution rate=total amount of eluted protein/ total amount of imprinted protein, in which the total amount of imprinted protein was 100 mg, and the elution rate was 97.8%. Finally, the imprinted polymer was washed with deionized water to remove residual sodium chloride.

Figure 1:
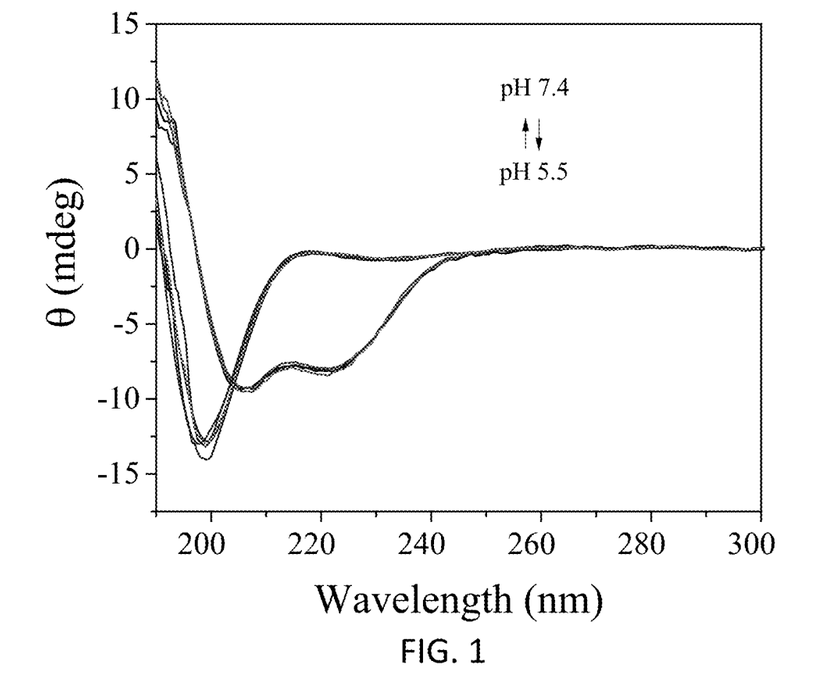
FIG. 1 is CD spectra of the peptide-crosslinked protein-imprinted polymer in example 1 under different conditions showing a reversible helix-coil transition of the peptide chain in the polymer.
Figure 2:
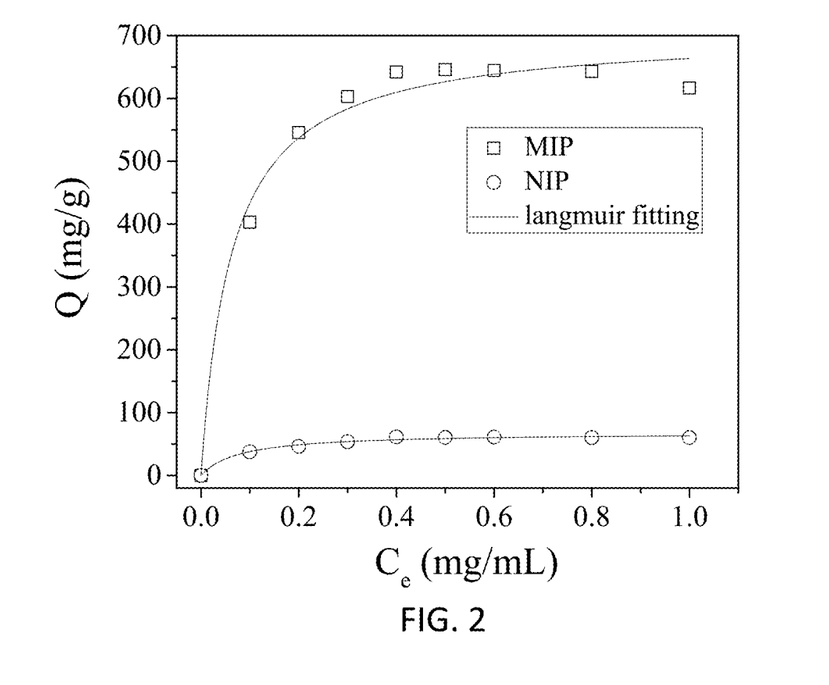
FIG. 2 is adsorption isotherms of the template protein on peptide-crosslinked protein-imprinted polymer (MIP) and the corresponding non-imprinted polymer (NIP).

Study of Imprint Effect:

A various concentrations of lysozyme solutions were formulated with a 20 mM pH 5.5 phosphate buffer solution. MIP or NIP was added at 37° C. After thorough adsorption, an ultraviolet spectrophotometer was used to detect the concentration of lysozyme in the supernatant and calculate adsorption amount. The calculation of adsorption amount was performed using a conventional calculation method in the art, see reference Z. Hua, et al. Langmuir, 2008, 24, 5773-5780. The adsorption isotherms (adsorption amount v.s. equilibrium concentration of protein) were drawn, and theses curves were fitted by Langmuir model. The results showed that the adsorption capacity Qm and imprinting factor of MIP were 679 mg/g dry gel and 10.0, respectively. The formula of this embodiment was the same as that of the reference (Z. Chen, et al. Journal of Molecular Recognition, 2008, 21(1), 71-77), except that an equal molar amount of peptide crosslinking agent was used to replace the crosslinking agent used in the reference. The adsorption capacity Qm and imprinting factor of the imprinted polymer described in the reference (Z. Chen, et al. Journal of Molecular Recognition, 2008, 21(1), 71-77) were 350 mg/g dry gel and 1.167, respectively. As compared to the reference, the imprint effect of the imprinted polymer prepared by this embodiment was improved significantly.

Figure 3:
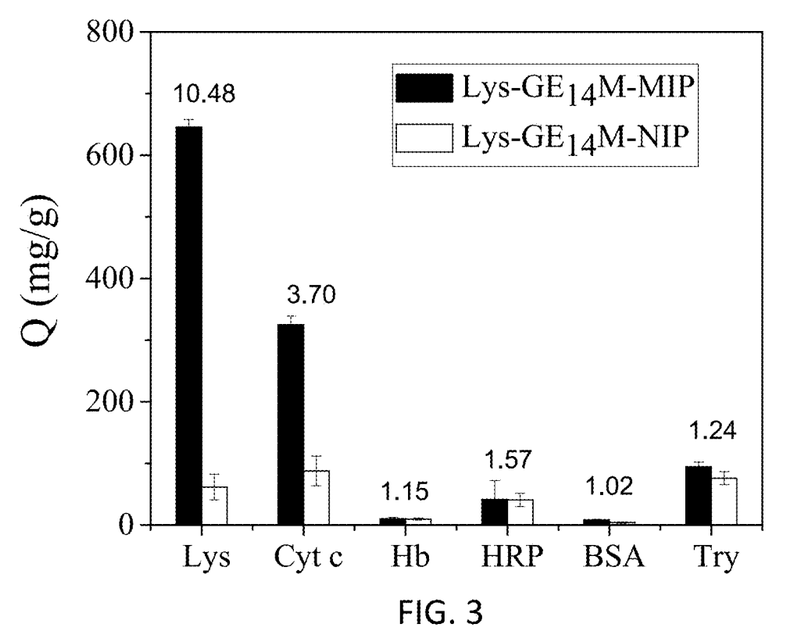
FIG. 3 is adsorption of lysozyme (Lys), the template protein, and various other proteins on the peptide-crosslinked protein-imprinted polymer (MIP) and the corresponding non-imprinted polymer (NIP).

20 mM of a pH 5.5 phosphate buffer solution was used to prepare various protein solutions with a concentration of 0.4 mg/mL, including lysozyme, cytochrome C (Cyt C), hemoglobin (Hb), horseradish peroxidase (HRP), bovine serum albumin (BSA), trypsin inhibitor (Try). MIP or NIP was added at 37° C. After thorough adsorption, the absorbance value of supernatant was detected by UV and the adsorption amount was calculated. The imprinting factors of various proteins were 10.48 (Lysozyme), 3.70 (Cyt C), 1.15 (Hb), 1.57 (HRP), 1.02 (BSA), and 1.24 (Try), indicating that the imprinted polymer can selectively adsorb lysozyme.

Comparative Example 1

The synthesis of imprinted polymers:

200 mg of N-isopropylacrylamide, 5 mg of acrylamide, 4 µL of methacrylic acid, 9 mg N, N'-methylenebisacrylamide (BIS), and 100 mg of template protein lysozyme were dissolved in 2 mL of a 20 mM pH 5.5 phosphate buffer solution. After thorough mixing, 50 µL of 10% APS and 5 µL of TEMED were added to initiate polymerization, and the reaction was carried out at 37° C. for 24 hours to obtain the imprinted polymer MIP. The preparation of non-imprinted polymer NIP is the same as that of imprinted polymer, except that no template protein lysozyme is added. The formula was completely the same as that of the reference (Z. Chen, et al. Journal of Molecular Recognition, 2008, 21(1), 71-77). The only difference was that the peptide crosslinking agent was replaced by an equal molar amount of a common cross-linking agent N, N'-methylenebisacrylamide as compared to the formula of imprinted polymer in example 1.

The Elution of Template Protein:

Protein elution was performed at 37° C. with a 20 mM pH 7.4 phosphate buffer solution (containing 0.154 M NaCl to simulate physiological ionic strength). The first elution rate was 35.77%, the second elution rate was 5.52%, the third elution rate was 2.85%, and the fourth elution rate was 0. The total elution rate was 44.14%. The results indicated that more than half of the template proteins could not be eluted under this condition. Whereas, for the peptide-crosslinked imprinted polymers prepared in example 1, the template protein was able to be completely eluted under the same condition.

To compare with the imprint experiments of the protein-imprinted polymer synthesized with the peptide crosslinking agent, the proteins were eluted with a 20 mM pH7.4 phosphate buffer solution containing 1M NaCl at 37° C. until the remaining template proteins were completely eluted.

Study of Imprint Effect:

MIP was protein-eluted with a 20 mM pH 7.4 phosphate buffer solution containing 1 M NaCl to completely remove the template protein. A various concentrations of lysozyme solutions were formulated with a 20 mM pH 5.5 phosphate buffer solution. MIP or NIP was added at 37° C. After thorough adsorption, an ultraviolet spectrophotometer was used to detect the concentration of lysozyme in the supernatant and calculate adsorption amount. The calculation of adsorption amount was performed using a conventional calculation method in the art, see reference Z. Hua, et al. Langmuir, 2008, 24, 5773-5780. The adsorption isotherms (adsorption amount v.s. equilibrium concentration of protein) were drawn, and theses curves were fitted by Langmuir model. The results showed that the adsorption capacity Qm of MIP was 387.0 mg/g dry gel, and the maximum adsorption capacity Qm of NIP were 210.9 mg/g dry gel, and imprinting factor was 1.83. The results were similar to the results reported in the reference (Z. Chen, et al. Journal of Molecular Recognition, 2008, 21(1), 71-77).

The formula of comparative example 1 was substantially the same as that of example 1, the only difference is that comparative example 1 used a common crosslinking agent N, N-methylenebisacrylamide, while example 1 used an equal molar amount of the peptide crosslinking agent. It can be seen that the use of peptide crosslinking agent not only can achieve complete removal of template protein under mild conditions and can also improve imprint effect significantly.

Example 2

The Synthesis of Imprinted Polymer:

200 mg of N-isopropylacrylamide, 2.5 mg of acrylamide, 8 µL of dimethylaminoethyl methacrylate, 115 mg of the peptide crosslinking agent, and 100 mg of template protein bovine serum albumin (BSA) were dissolved in 2 mL of 20 mM pH 5.5 phosphate buffer solution. After thorough mixing, 50 µL of 10% APS and 5 µL of TEMED were added to initiate the polymerization. The reaction was carried out at 37° C. for 24 h to obtain the imprinted polymer MIP. The preparation of non-imprinted polymer NIP is the same as that of imprinted polymer, except that no template protein bovine serum albumin is added. The structure of peptide crosslinking agent is the same as that in example 1.

The Elution of Template Protein:

Protein elution was performed at 37° C. with a 20 mM pH 7.4 phosphate buffer solution (containing 0.154 M NaCl to simulate physiological ionic strength), and four elution rates were 95.24%, 2.05%, 0.24%, 0%, respectively. The total elution rate was 97.51%. Finally, the imprinted polymer was washed with deionized water to remove residual salts.

Study of Imprint Effect:

A various concentrations of BSA solutions were formulated with a 20 mM pH 5.5 phosphate buffer solution. MIP or NIP was added at 37° C. After thorough adsorption, an ultraviolet spectrophotometer was used to detect the concentration of template protein bovine serum albumin in the supernatant. The adsorption isotherms (adsorption amount v.s. equilibrium concentration of protein) were drew, and theses curves were fitted by Langmuir model. The results showed that the maximum adsorption capacity Qm of MIP was 420.3 mg/g dry gel, the maximum adsorption capacity Qm of NIP was 54.4 mg/g dry gel, the imprinting factor was 7.72.

Comparative Example 2

The Synthesis of Imprinted Polymers:

200 mg of N-isopropylacrylamide, 2.5 mg of acrylamide, 8 μL of dimethylaminoethyl methacrylate, 9 mg of N, N'-methylenebisacrylamide, and 100 mg of template protein bovine serum albumin (BSA) were dissolved in 2 mL of a 20 mM pH 5.5 phosphate buffer solution. After thorough mixing, 50 μl of 10% APS and 5 μL of TEMED were added to initiate the polymerization. The reaction was carried out at 37° C. for 24 h to obtain the imprinted polymer MIP. The preparation of non-imprinted polymer NIP is the same as that of imprinted polymer, except that no template protein bovine serum albumin was added.

The Elution of Template Protein:

Protein elution was performed at 37° C. with a 20 mM pH 7.4 phosphate buffer solution (containing 0.154 M NaCl to simulate physiological ionic strength). The first elution rate was 54.77%, the second elution rate was 6.96%, the third elution rate was 0.75%, and the fourth elution rate was 0. The total elution rate was 62.48%. The results indicated that there were substantial template proteins could not be eluted under this condition. Whereas, for the peptide-crosslinked imprinted polymers prepared in embodiment 2, the template proteins was able to be completely eluted under the same condition.

The proteins were eluted with a 20 mM pH 7.4 phosphate buffer solution containing 1M NaCl at 37° C. until the template proteins were completely eluted.

Study of Imprint Effect:

MIP was protein-eluted with a 20 mM pH 7.4 phosphate buffer solution containing 1 M NaCl to completely remove the template protein. A various concentrations of BSA solutions were formulated with a 20 mM pH 5.5 phosphate buffer solution. MIP or NIP was added at 37° C. After thorough adsorption, an ultraviolet spectrophotometer was used to detect the concentration of template protein bovine serum albumin in the supernatant and to calculate the adsorption amount. The adsorption isotherms (adsorption amount v.s. equilibrium concentration of protein) were drew, and theses curves were fitted by Langmuir model. The results showed that the maximum adsorption capacity Qm of MIP was 214.7 mg/g dry gel, and the maximum adsorption capacity Qm of NIP was 126.3 mg/g dry gel, the imprinting factor was 1.69.

The formula of comparative example 2 was substantially the same as that of example 2, the only difference is that comparative example 2 used a common crosslinking agent N, N-methylenebisacrylamide, while example 2 used an equal molar amount of the peptide crosslinking agent. It can be seen that the use of peptide crosslinking agent not only can completely remove template protein under mild conditions and can also improve imprint effect significantly.

Example 3

The Synthesis of Imprinted Polymers:

200 mg of N-isopropylacrylamide, 5 mg of acrylamide, 4 μL of methacrylic acid, 51.74 mg of the peptide crosslinking agent, and 100 mg of template protein cytochrome C (Cyt C) were dissolved in 2 mL of 20 mM pH 5.5 phosphate buffer solution. After thorough mixing, 50 μL of 10% APS and 5 μL of TEMED were added to initiate the polymerization. The reaction was carried out at 37° C. for 24 h to obtain the imprinted polymer MIP. The preparation of non-imprinted polymer NIP was the same as that of imprinted polymer, except that no template protein cytochrome C was added. The structure of peptide crosslinking agent is the same as that in example 1.

The Elution of Template Protein:

Protein elution was performed at 37° C. with a 20 mM pH 7.4 phosphate buffer solution (containing 0.154 M NaCl to simulate physiological ionic strength), and four elution rates were 93.40%, 2.06%, 1.34%, 0%, respectively. The total elution rate was 96.8%. Finally, the imprinted polymer was washed with deionized water to remove residual salts.

Study of Imprint Effect:

A various concentrations of Cyt C solutions were formulated with a 20 mM pH 5.5 phosphate buffer solution. MIP or NIP was added at 37° C. After thorough adsorption, an ultraviolet spectrophotometer was used to detect the concentration of template protein cytochrome C in the supernatant. The adsorption isotherms (adsorption amount v.s. equilibrium concentration of protein) were drawn, and theses curves were fitted by Langmuir model. The results showed that the maximum adsorption capacity Qm of MIP was 562.0 mg/g dry gel, and the maximum adsorption capacity Qm of NIP was 79.6 mg/g dry gel, and imprinting factor was 7.1.

Comparative Example 3

The Synthesis of Imprinted Polymers:

200 mg of N-isopropylacrylamide, 5 mg of acrylamide, 4 μL of methacrylic acid, 4 mg of N, N'-methylenebisacrylamide, and 100 mg of template protein cytochrome C (Cyt C) were dissolved in 2 mL of 20 mM pH 5.5 phosphate buffer solution. After thorough mixing, 50 μl of 10% APS and 5 μL of TEMED were added to initiate the polymerization. The react was carried out at 37° C. for 24 h to obtain the imprinted polymer MIP. The preparation of non-imprinted polymer NIP was the same as that of imprinted polymer, except that no template protein cytochrome C was added.

The Elution of Template Protein:

Protein elution was performed at 37° C. with a 20 mM pH 7.4 phosphate buffer solution (containing 0.154 M NaCl to simulate physiological ionic strength). The first elution rate was 48.32%, the second elution rate was 5.85%, the third elution rate was 2.59%, and the fourth elution rate was 0. The total elution rate was 56.76%. The results indicated that a substantial amount of template protein could not be eluted under this condition. Whereas, for the peptide-crosslinked imprinted polymers prepared in embodiment 3 template protein was able to be completely eluted the under the same condition.

The proteins were eluted with a 20 mM pH 7.4 phosphate buffer solution containing 1M NaCl at 37° C. until the template proteins were completely eluted.

Study of Imprint Effect:

MIP was protein-eluted with a 20 mM pH 7.4 phosphate buffer solution containing 1 M NaCl to completely remove the template protein. A various concentrations of Cyt C solutions were formulated with a 20 mM pH 5.5 phosphate buffer solution. MIP or NIP was added at 37° C. After thorough adsorption, an ultraviolet spectrophotometer was used to detect the concentration of template protein bovine serum albumin in the supernatant and to calculate the adsorption amount. The adsorption isotherms (adsorption amount v.s. equilibrium concentration of protein) were drew, and theses curves were fitted by Langmuir model. The results showed that the maximum adsorption capacity Qm of MIP was 328.4 mg/g dry gel, and the maximum adsorption capacity Qm of NIP was 236.4 mg/g dry gel, and imprinting factor was 1.39.

The formula of comparative example 3 was substantially the same as that of example 3, the only difference is that comparative example 3 used a common crosslinking agent N, N-methylenebisacrylamide, while example 3 used an equal molar amount of the peptide crosslinking agent. It can be seen that the use of peptide crosslinking agent not only can completely remove template protein under mild conditions and can also improve imprint effect significantly.

Example 4

The Synthesis of Imprinted Polymers:

200 mg of N-isopropylacrylamide, 5 mg of acrylamide, 4 μL of methacrylic acid, 150 mg of the peptide crosslinking agent, and 100 mg of template protein lysozyme (Lyz) were dissolved in 2 mL of 20 mM pH 5.0 phosphate buffer solution. After thorough mixing, 50 μL of 10% APS and 5 μL of TEMED were added to initiate the polymerization. The reaction was carried out at 37° C. for 24 h to obtain the imprinted polymer MIP. The preparation of non-imprinted polymer NIP was the same as that of imprinted polymer, except that no template protein lysozyme was added. The structure of the peptide crosslinking agent is as shown in Formula II:

The Elution of Template Protein:

Protein elution was performed at 37° C. with a 20 mM pH 7.4 phosphate buffer solution (containing 0.154 M NaCl to simulate physiological ionic strength), and the elution rate was 97.8%. Finally, the imprinted polymer was washed with deionized water to remove residual salts.

Study of Imprint Effect:

A various concentrations of lysozyme (Lyz) solutions were formulated with a 20 mM pH 5.0 phosphate buffer solution. MIP or NIP was added at 37° C. After thorough adsorption, an ultraviolet spectrophotometer was used to detect the concentration of template protein lysozyme in the supernatant and calculate adsorption amount, resulting an imprinting factor of 10.21.

Example 5

The Synthesis of Imprinted Polymers:

400 mg of N-isopropylacrylamide, 5 mg of acrylamide, 16 μL of N-[3-(dimethylamino) propyl]-methacrylamide (DMAPMA), 200 mg of the peptide crosslinking agent, and 100 mg of template protein BSA were dissolved in 2 mL of a 10 mM pH 10.0 Tris buffer solution. Deoxygenation was performed by nitrogen sparging for 30 min, and then 50 μL of 10% APS and 5 μL of TEMED were added to initiate the polymerization. The reaction was carried out at room temperature for 24 h to obtain the imprinted polymer MIP. The preparation of non-imprinted polymer NIP was the same as that of imprinted polymer, except that no template protein BSA was added. The structure of the peptide crosslinking agent is as shown in Formula III:

The Elution of Template Protein:

Protein elution was performed at 37° C. with a 10 mM pH 7.4 Tris buffer solution (containing 0.154 M NaCl to simulate physiological ionic strength), and the elution rate was 96.8%. Finally, the imprinted polymer was washed with deionized water to remove residual salts.

Study of Imprint Effect:

A various concentrations of BSA buffer solutions were formulated with a 10 mM pH 10.0 Tris buffer. MIP or NIP was added at 37° C. After thorough adsorption, an ultraviolet spectrophotometer was used to detect the concentration of template protein BSA in the supernatant and calculate adsorption amount, resulting an imprinting factor of 10.13.

Example 6

The synthesis of imprinted polymers: 400 mg of N-isopropylacrylamide, 5 mg of acrylamide, 16 μL of N-[3-

(dimethylamino) propyl]-methacrylamide (DMAPMA), 210 mg of the peptide crosslinking agent, and 100 mg of template protein BSA were dissolved in 2 mL of 10 mM pH 10.0 Tris buffer solution. Deoxygenation was performed by nitrogen sparging for 30 min, and then 50 μL of 10% APS and 5 μL of TEMED were added to initiate the polymerization. The reaction was carried out at room temperature for 24 h to obtain the imprinted polymer MIP. The preparation of non-imprinted polymer NIP was the same as that of imprinted polymer, except that no template protein BSA was added. The structure of the peptide crosslinking agent is as shown in Formula IV:

polymer, except that no template protein BSA was added. The structure of peptide crosslinking agent is the same as that in example 6.

The Elution of Template Protein:
Protein elution was performed at 25° C. with 0.154M NaCl solution, and the elution rate was 97.1%. Finally, the imprinted polymer was washed with deionized water to remove residual sodium chloride.

Study of Imprint Effect:
A various concentrations of BSA solutions were formulated with 2 mL 0.2 M NaClO₄ solution. MIP or NIP was added at 37° C. After thorough adsorption, an ultraviolet spectrophotometer was used to detect the concentration of template protein BSA in the supernatant and calculate adsorption amount, resulting an imprinting factor of 10.38.

The Elution of Template Protein:
Protein elution was performed at 37° C. with a 10 mM pH 7.4 Tris buffer solution (containing 0.154 M NaCl to simulate physiological ionic strength), and the elution rate was 98.2%. Finally, the imprinted polymer was washed with deionized water to remove residual salts.

Study of Imprint Effect:
A various concentrations of BSA buffer solutions were formulated with a 10 mM pH 10.0 Tris buffer. MIP or NIP was added at 37° C. After thorough adsorption, an ultraviolet spectrophotometer was used to detect the concentration of template protein BSA in the supernatant and calculate adsorption amount, resulting an imprinting factor of 10.96.

Example 7

The Synthesis of Imprinted Polymers:
400 mg of N-isopropylacrylamide, 5 mg of acrylamide, 16 μL of N-[3-(dimethylamino) propyl]-methacrylamide (DMAPMA), 210 mg of the peptide crosslinking agent, and Example 8

The Synthesis of Imprinted Polymers:
400 mg of N-isopropylacrylamide, 5 mg of acrylamide, 16 μL of N-[3-(dimethylamino)propyl]-methacrylamide (DMAPMA), 200 mg of the peptide crosslinking agent, and 100 mg of template protein BSA were dissolved in a 10 mM pH 7.0 Tris buffer solution in an ice water bath. Deoxygenation was performed by nitrogen sparging for 30 min, and then 50 μL of 10% APS and 5 μL of TEMED were added to initiate the polymerization. The reaction was carried out at 0° C. for 24 h to obtain the imprinted polymer MIP. The preparation of non-imprinted polymer NIP was the same as that of imprinted polymer, except that no template protein BSA was added. The structure of the peptide crosslinking agent is as shown in Formula V:

100 mg of template protein BSA were dissolved in 2 mL of a 0.2M NaClO₄ solution. Deoxygenation was performed by nitrogen sparging for 30 min, and then 50 μL of 10% APS and 5 μL of TEMED were added to initiate the polymerization. The reaction was carried out at 25° C. for 24 h to obtain the imprinted polymer MIP. The preparation of non-imprinted polymer NIP was the same as that of imprinted The Elution of Template Protein:
Protein elution was performed at 37° C. with a 10 mM pH 7.0 Tris buffer solution, and the elution rate was 98.8%. Finally, the imprinted polymer was washed with deionized water to remove residual sodium chloride.

Study of Imprint Effect:
A various concentrations of Tris solutions were formulated with a 2 mL 10 mM pH 7.0 Tris buffer solution. MIP or NIP was added at 0° C. After thorough adsorption, an ultraviolet spectrophotometer was used to detect the concentration of template protein BSA in the supernatant and calculate adsorption amount, resulting an imprinting factor of 10.87.

Example 9

The Synthesis of Imprinted Polymers:

400 mg of N-isopropylacrylamide, 5 mg of acrylamide, 16 μL of N-[3-(dimethylamino)propyl]-methacrylamide (DMAPMA), 210 mg of the peptide crosslinking agent, and 100 mg of template protein BSA were dissolved in a 10 mM pH 7.0 Tris buffer solution in an ice water bath. Deoxygenation was performed by nitrogen sparging for 30 min, and then 50 μL of 10% APS and 5 μL of TEMED were added to initiate the polymerization. The reaction was carried out at 0° C. for 24 h to obtain the imprinted polymer MIP. The preparation of non-imprinted polymer NIP was the same as that of imprinted polymer, except that no template protein BSA was added. The structure of the peptide crosslinking agent is as shown in Formula VI:

The Elution of Template Protein:

Protein elution was performed at 37° C. with a 10 mM pH 7.0 Tris buffer solution, and the elution rate was 97.2%. Finally, the imprinted polymer was washed with deionized water to remove residual sodium chloride.

Study of Imprint Effect:

A various concentrations of Tris solutions were formulated with a 2 mL 10 mM pH 7.0 Tris buffer solution. MIP or NIP was added at 0° C. After thorough adsorption, an ultraviolet spectrophotometer was used to detect the concentration of template protein BSA in the supernatant and calculate adsorption amount, resulting an imprinting factor of 10.96.

Example 10

The Synthesis of Imprinted Polymers:

200 mg of N-isopropylacrylamide, 5 mg of acrylamide, 4 μL of methacrylic acid, 115 mg of the peptide crosslinking agent, and 100 mg of template protein lysozyme were dissolved in 2 mL of a 20 mM pH 5.5 phosphate buffer solution. After thorough mixing, 50 μL of 10% APS and 5 μL of TEMED were added to initiate polymerization, and the reaction was carried out at 37° C. for 24 hours to obtain the imprinted polymer MIP. The structure of the peptide crosslinking agent is as shown in Formula I.

The elution and recover of template protein:

The elution of template protein by lysozyme was performed with two different solutions at 37° C. The first solution was a 20 mM pH 7.4 phosphate buffer solution containing 0.154M NaCl, and the second solution was a 20 mM pH 7.4 phosphate buffer solution containing 1M NaCl. The eluent was desalted via dialysis and freeze dried to obtain the recovered template protein lysozyme.

The circular dichroism of recovered lysozyme sample was determined and compared to that of original sample. Negligible changes in the secondary and tertiary structure of the protein eluted and recovered with a 20 mM pH 7.4 phosphate buffer solution containing 0.154 M NaCl were observed. However, for the protein eluted and recovered with a 20 mM pH 7.4 phosphate buffer solution containing 1 M NaCl, significantly changes in the secondary and tertiary structure were found. The results showed that a protein elution performed at mild conditions has little influence on higher structure of proteins, while a protein elution performed with a solution containing a high concentration of salt will cause a destruction of proteins.

Figure 4:
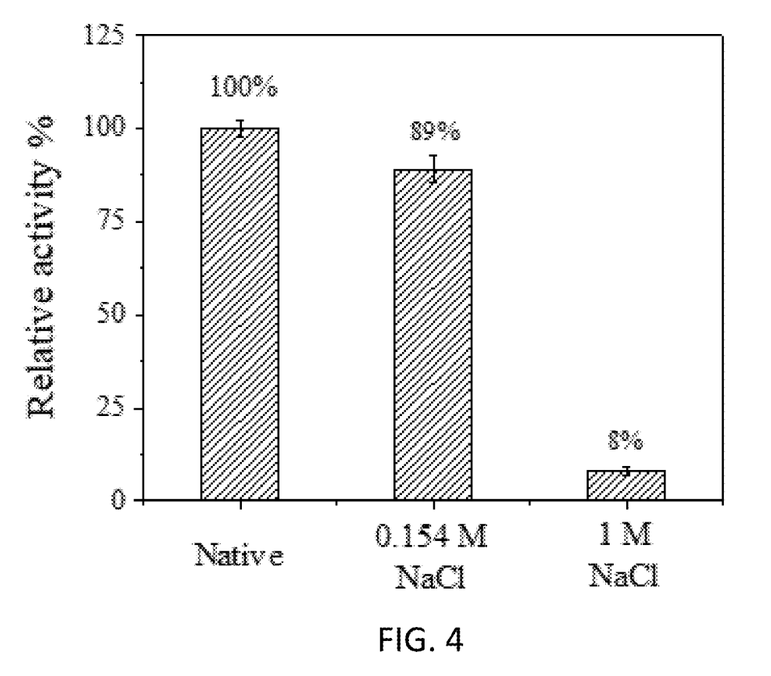
FIG. 4 is the bioactivities of lysozyme samples (related to native lysozyme) which samples were eluted using a low-salt eluant and a high salt eluant.

The bioactivity of two recovered lysozyme samples was determined using *Micrococcus luteus* as a substrate and compared to bioactivity of original sample. The activity of the lysozyme sample eluted at mild conditions was still up to 89%, while the activity of the lysozyme sample eluted with a solution containing a high concentration of salt was only 8%. It was showed that performing template protein-elution at mild conditions is favorable to preserve the activity of target protein.

Example 11

Lysozyme was extracted from egg while with the lysozyme-imprinted polymer synthesized in example 1. Egg white is known to contain 148 kinds of proteins, and the lysozyme content is 3-3.5%.

Figure 5:
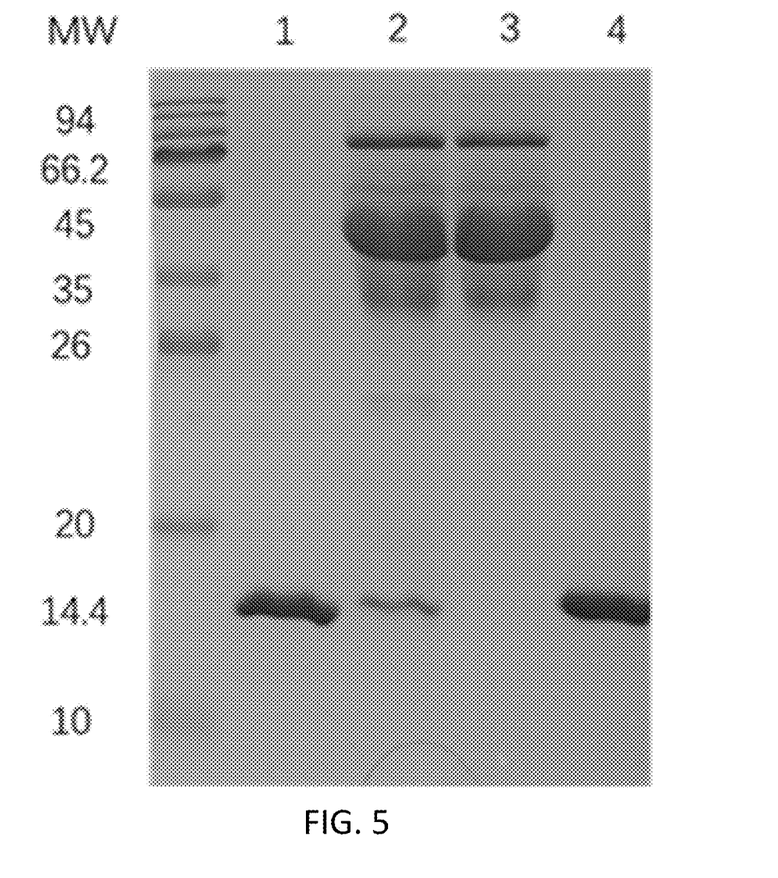
FIG. 5 is results of SDS-PAGE analysis of the lysozymes extracted from egg white, in which the first lane is a lysozyme specimen, the second lane is an untreated egg white sample, the third lane is an egg white sample treated with the peptide-crosslinked protein-imprinted polymer, and the fourth lane is an eluent sample obtained by treating egg white with the peptide-crosslinked protein-imprinted polymer followed by elution with a low-salt eluent.

Extraction of Lysozyme from Egg White:

Fresh egg white was diluted by 20 times with a 20 mM pH 5.5 phosphate buffer solution. 20 mg of the imprinted polymer was added and incubated at 37° C. for 10 h. The imprinted polymer was removed out and eluted with a 20 mM pH 7.4 phosphate buffer solution containing 0.154M NaCl to recover the adsorbed lysozyme protein. The extraction results were analyzed by SDS-PAGE. The first lane is a lysozyme specimen, the second lane is an untreated egg white sample, the third lane is an egg white sample treated with the imprinted polymer, and the fourth lane is an eluent sample of the imprinted polymer. The results showed that the lysozyme-imprinted polymer synthesized in example 1 can selectively extract lysozyme from egg while. The results were analyzed by HPLC, and it was also confirmed that the lysozyme-imprinted polymer synthesized in example 1 can selectively extract lysozyme from egg while. And it can be seen from HPLC results that the recovery rate was up to 96.3% and the product purity reached 93.4% by using this method.

The bioactivity of the extracted lysozyme sample was determined using *Micrococcus luteus* as a substrate and its relative activity was 92% (relative to an original commercial sample).

It can be known from the above examples that, the preparation method of the peptide-crosslinked protein-imprinted polymer provided in the invention conducts polymerization when the peptide crosslinking agent exists in a helix conformation and template-elution when the peptide chain exists in a coil conformation. The template protein can be removed under mild conditions. The size and spatial configuration of imprinting sites in the protein-imprinted polymer can completely recover and thus can specifically recognize the target protein. The peptide-crosslinked protein-imprinted polymers provided in the invention not only can completely remove the template protein under mild conditions, but also can significantly improve the imprint effect of the protein-imprinted polymer.

It should be noted that, the above is only preferred embodiments of the invention, those of ordinary skill in the art can make several improvements and modifications without departing from the principle of the invention, which improvements and modifications should be regarded as the protection scope of the invention.

What is claimed is:

1. A method of preparing a peptide-crosslinked protein-imprinted polymer comprising:
    dissolving a main monomer, functional monomers, a peptide crosslinking agent, and a template protein in an aqueous solution to obtain a mixed solution;
    adding an initiator or initiator system to the mixed solution to initiate the polymerization while the peptide crosslinking agent exists in a helix conformation, thereby obtaining a polymer;
    eluting the template protein while the peptide chain exists in a coil conformation, thereby obtaining a peptide-crosslinked protein-imprinted polymer;
    wherein the peptide crosslinking agent is a peptide with a polymerizable double bond at both ends, the peptide crosslinking agent being capable of undergoing a helix-coil transition.

2. The method according to claim 1, wherein the peptide crosslinking agent comprises a quantity of amino acids from 2 to 100.

3. The method according to claim 1, wherein the peptide crosslinking agent comprises a quantity of amino acids from 5 to 30.

4. The method according to claim 3, wherein the aqueous solution comprises one of a phosphate buffer, a Tris buffer, and a $NaClO_4$ solution.

5. The method according to claim 1, wherein the aqueous solution comprises one of a phosphate buffer, a Tris buffer, and a $NaClO_4$ solution.

6. The method according to claim 1, wherein the mixed solution comprises a mass ratio of ranges of the main monomer: the functional monomers: the peptide crosslinking agent: the template protein of (10-30):(0.5-2):(5-20):(5-20).

7. The method according to claim 1, wherein the initiator is selected from the group consisting of: a combination of ammonium persulfate solution and tetramethylethylenediamine, a combination of ammonium persulfate solution and sodium bisulfite, a combination of potassium persulfate solution and tetramethylethylenediamine, and a combination of potassium persulfate solution and sodium bisulfite.

8. The method according to claim 1, further comprising detecting a conformational state of the peptide crosslinking agent by circular dichroism (CD), in which:
    a CD spectrum presents a negative peak at 222 nm and 208 nm, and a positive peak at 190 nm±5 nm representative of a helix conformation; and
    a CD spectrum presents a negative peak at 199 nm, and a positive peak at 220 nm±5 nm representative of a coil conformation.

9. A peptide-crosslinked protein-imprinted polymer prepared by a method comprising:
    dissolving a main monomer, functional monomers, a peptide crosslinking agent, and a template protein in an aqueous solution to obtain a mixed solution;
    adding an initiator or initiator system to the mixed solution to initiate the polymerization while the peptide crosslinking agent exists in a helix conformation, thereby obtaining a polymer;
    eluting the template protein while the peptide chain exists in a coil conformation, thereby obtaining a peptide-crosslinked protein-imprinted polymer;
    the peptide crosslinking agent is a peptide with a polymerizable double bond at both ends, the peptide crosslinking agent being capable of undergoing a helix-coil transition, wherein the peptide-crosslinked protein-imprinted polymer comprises a polypeptide-crosslinked protein-imprinted polymer.

10. A method for protein enrichment, separation, or purification, comprising absorbing a target protein while the peptide chain exists in a helix conformation with the polypeptide crosslinked protein imprinted polymer according to claim 9, and eluting the target protein when the peptide chain exists in a coil conformation.

* * * * *